United States Patent
Jogasaki et al.

(10) Patent No.: US 10,085,728 B2
(45) Date of Patent: Oct. 2, 2018

(54) TREATMENT-TOOL DRIVING DEVICE (71) Applicant: OLYMPUS CORPORATION, Tokyo (JP)

(72) Inventors: Shuya Jogasaki, Tokyo (JP); Toshihiro Yoshii, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/413,720

(22) Filed: Jan. 24, 2017

(65) Prior Publication Data

US 2017/0156711 A1 Jun. 8, 2017

Related U.S. Application Data (63) Continuation of application No. PCT/JP2015/071288, filed on Jul. 27, 2015.

(30) Foreign Application Priority Data

Jul. 28, 2014 (JP) ................................. 2014-152518

(51) Int. Cl.
*B25J 17/00* (2006.01)
*B25J 17/02* (2006.01)
(Continued)

(52) U.S. Cl.
CPC ... *A61B 17/00234* (2013.01); *A61M 25/0113* (2013.01); *A61B 2017/0046* (2013.01);
(Continued)

(58) Field of Classification Search
CPC ................................ B25J 9/104; B25J 9/1045; A61B 2017/00327
See application file for complete search history.

(56) References Cited

U.S. PATENT DOCUMENTS 4,203,430 A * 5/1980 Takahashi ............ A61B 1/0052
403/43
8,333,780 B1 * 12/2012 Pedros ................... A61B 17/29
600/37
(Continued)

FOREIGN PATENT DOCUMENTS

EP 2 687 166 A2 1/2014
EP 2 799 019 A1 11/2014
(Continued)

OTHER PUBLICATIONS

International Search Report dated Oct. 20, 2015 issued in PCT/JP2015/071288.
(Continued)

*Primary Examiner* — Jake Cook
(74) *Attorney, Agent, or Firm* — Scully, Scott, Murphy & Presser, P.C.

(57) ABSTRACT

A treatment-tool driving device being attached to a treatment tool provided with at least one pair of tensile-force transmitting members and driving the treatment tool by tensile forces imparted to the tensile-force transmitting members, wherein the device includes: movable members being individually attached to one ends of the individual tensile-force transmitting members; a driving source generating a motive power with which the treatment tool is driven; a motive-power transmitting mechanism switching between coupling and decoupling between the driving source and the movable members, and transmitting, in a coupled state, the motive power from the driving source so as to selectively impart tensile forces to the two movable members attached to the paired tensile-force transmitting members; and a biasing portion biasing the two movable members in directions in which tensile forces are imparted to the tensile-force trans-
(Continued)

mitting members in a state in which coupling by the motive-power transmitting mechanism is released.

7 Claims, 10 Drawing Sheets

(51) Int. Cl.
*B25J 18/00* (2006.01)
*A61B 17/00* (2006.01)
*A61M 25/01* (2006.01)

(52) U.S. Cl.
CPC .............. *A61B 2017/00327* (2013.01); *A61B 2017/00398* (2013.01); *A61B 2017/00407* (2013.01); *A61B 2017/00411* (2013.01); *A61M 2025/015* (2013.01)

(56) References Cited

U.S. PATENT DOCUMENTS

| | | | |
|---|---|---|---|
| 2002/0082617 A1* | 6/2002 | Nishtala | A61B 17/32056 606/139 |
| 2010/0082041 A1 | 4/2010 | Prisco | |
| 2014/0005678 A1 | 1/2014 | Shelton, IV et al. | |
| 2014/0025046 A1 | 1/2014 | Williams et al. | |
| 2014/0249545 A1 | 9/2014 | Hyodo et al. | |
| 2016/0000513 A1 | 1/2016 | Shelton, IV et al. | |
| 2016/0166342 A1 | 6/2016 | Prisco | |
| 2016/0302790 A1 | 10/2016 | Williams et al. | |
| 2016/0331375 A1 | 11/2016 | Shelton, IV et al. | |

FOREIGN PATENT DOCUMENTS

| | | |
|---|---|---|
| EP | 2 982 314 A1 | 2/2016 |
| JP | S62-254726 A | 11/1987 |
| JP | H06-130307 A | 5/1994 |
| JP | H11-099124 A | 4/1999 |
| JP | 2002-200091 A | 7/2002 |
| JP | 2010-200892 A | 9/2010 |
| JP | 2012-504016 A | 2/2012 |
| JP | 2013-103074 A | 5/2013 |
| JP | 2013-215508 A | 10/2013 |
| JP | 2014-039809 A | 3/2014 |
| JP | 2014-079653 A | 5/2014 |
| JP | 2014-193417 A | 10/2014 |
| JP | 2017-018628 A | 1/2017 |
| WO | WO 2010/039387 A1 | 4/2010 |
| WO | 2014/004293 A1 | 1/2014 |

OTHER PUBLICATIONS

Extended Supplementary European Search Report dated Feb. 14, 2018 in European Patent Application No. 15 82 8121.2.

\* cited by examiner

TREATMENT-TOOL DRIVING DEVICE

CROSS-REFERENCE TO RELATED APPLICATIONS

This is a continuation of International Application PCT/JP2015/071288 which is hereby incorporated by reference herein in its entirety.

This application is based on Japanese Patent Application No. 2014-152518, the contents of which are incorporated herein by reference.

TECHNICAL FIELD

The present invention relates to a treatment-tool driving device.

BACKGROUND ART

There is a known wire-coupling tool in which wires for bending a bending portion provided at a distal end of an inserted portion of an endoscope are separated into those on the operating-portion side and those on the bending-portion side, and are individually connected in an attachable/detachable manner by using connectors (for example, see Patent Literature 1).

With this wire-coupling tool, the wires on the bending-portion side are held by first holding portions at proximal-end portions thereof, the connectors attached to the distal ends of the wires on the operating-portion side are held by second holding portions, and, by removing the holding portions after connecting the two wires by bringing the two associated holding portions close to each other, the two wires are kept in connected states by means of the connectors.

CITATION LIST

Patent Literature

{PTL 1} Japanese Unexamined Patent Application, Publication No. 2010-200892

SUMMARY OF INVENTION

Solution to Problem

An aspect of the present invention is a treatment-tool driving device that is attached, in an attachable/detachable manner, to a treatment tool provided with at least one pair of tensile-force transmitting members and that drives the treatment tool by means of tensile forces imparted to the tensile-force transmitting members, the treatment-tool driving device including: movable members that are individually attached, in an attachable/detachable manner, to one ends of the individual tensile-force transmitting members; a driving source that generates motive power with which the treatment tool is driven; a motive-power transmitting mechanism that switches between coupling and decoupling between the driving source and the movable members, and that transmits, in a coupled state, the motive power from the driving source so as to selectively impart tensile forces to the two movable members attached to the paired tensile-force transmitting members; and a biasing portion that biases the two movable members in directions in which tensile forces are imparted to the tensile-force transmitting members in a state in which coupling by the motive-power transmitting mechanism is released.

DESCRIPTION OF EMBODIMENT

A treatment-tool driving device 1 according to an embodiment of the present invention will be described below with reference to the drawings.

The treatment-tool driving device 1 according to this embodiment is a device that drives a treatment tool 3 provided with one or more joints or an end effector that are/is driven by two wires (tensile-force transmitting members) 2, which form a pair.

For example, the joints of the treatment tool 3 are configured to be driven by tensile forces that are selectively imparted to the two wires 2 so as to be flexed in one direction when one of the wires 2 is pulled, and so as to be flexed in the other direction when the other wire 2 is pulled.

In describing this embodiment, although a form in which the treatment tool 3 is simplified, having one pair of wires 2, will be described as an example, the present invention may be applied to a treatment tool 3 having multiple pairs of wires 2. In addition, examples of the end effector include gripping forceps, scissors forceps, or the like, and, in addition, an observing means such as a camera or the like.

Figure 1:
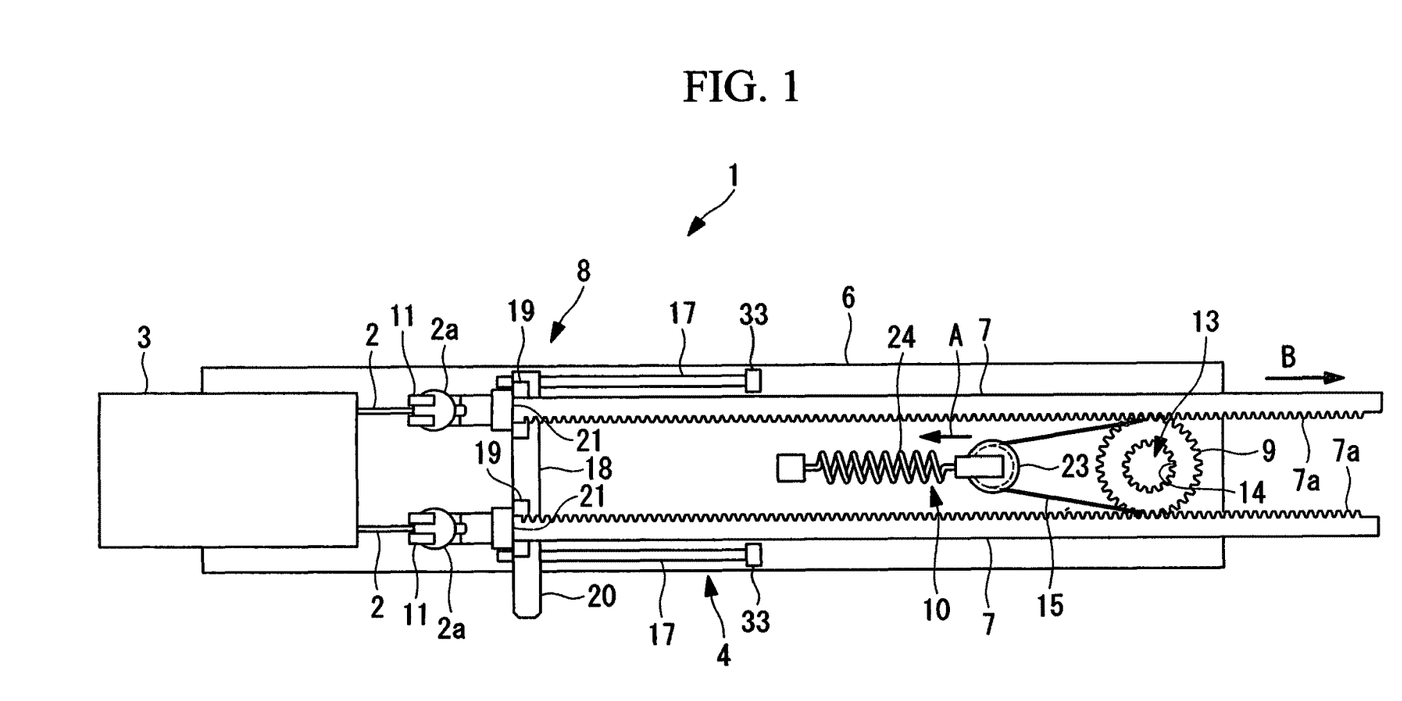
FIG. 1 is a plan view showing a treatment-tool driving device according to an embodiment of the present invention.
Figure 2:
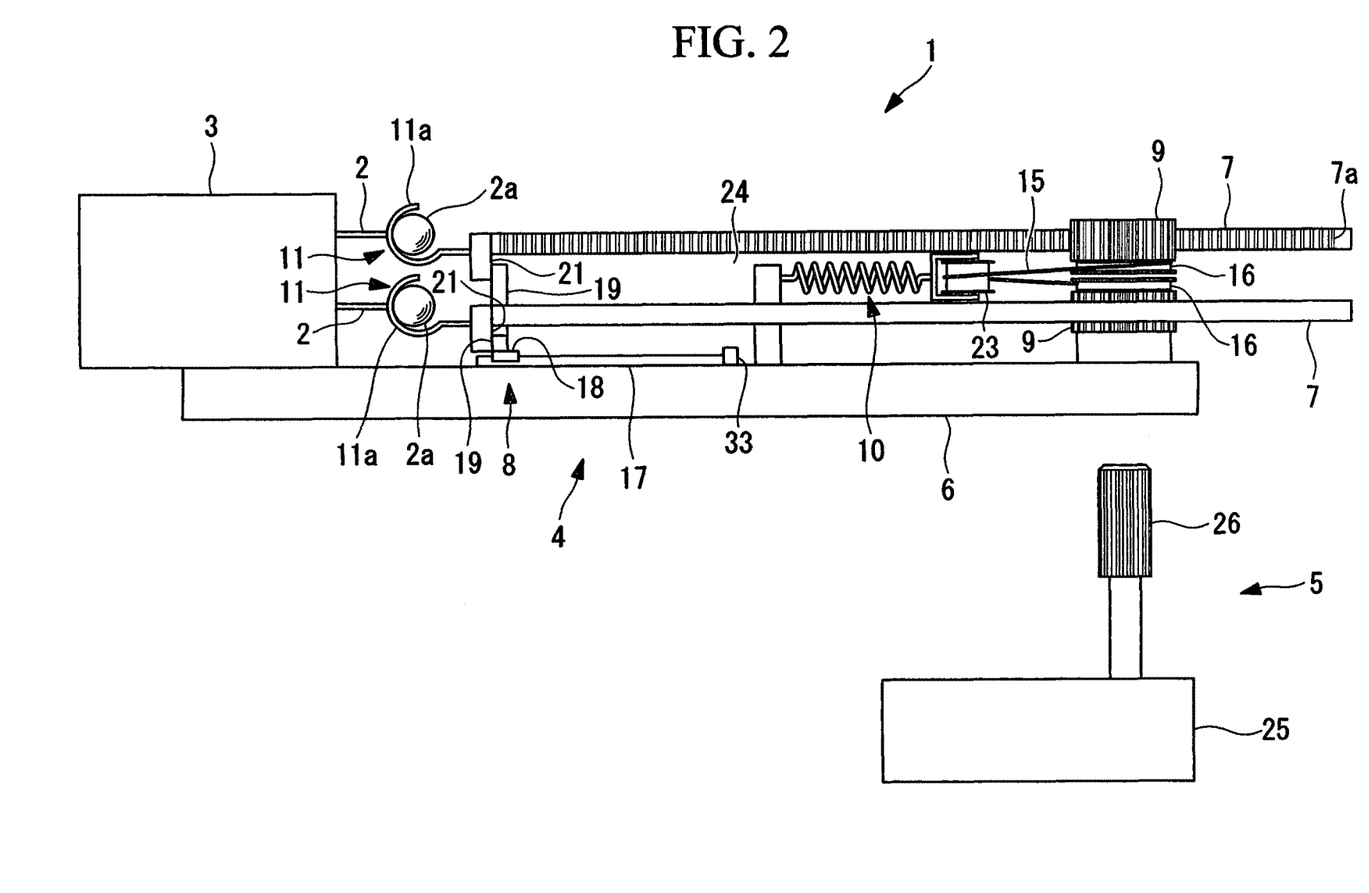
FIG. 2 is a front view showing the treatment-tool driving device in FIG. 1 in a state in which a driving portion is separated.

As shown in FIGS. 1 and 2, the treatment-tool driving device 1 according to this embodiment is provided with: an intermediate-mechanism portion 4 that is attached to the treatment tool 3 in an attachable/detachable manner; and a driving portion 5 that is attached to the intermediate-mechanism portion 4 in an attachable/detachable manner.

Spherical bodies 2a are secured to end portions of the two wires 2, which form a pair, of the treatment tool 3.

The intermediate-mechanism portion 4 is provided with: a base 6; two rack gears 7 that are disposed on a surface of the base 6 so as to be parallel to each other and that are supported so as to be movable in longitudinal directions; an alignment mechanism 8 that places the rack gears 7 by aligning end portions thereof; two pinion gears 9 that individually engage with the rack gears 7; and a biasing portion 10 that biases the pinion gears 9 so as to be rotated in one direction. A mechanism that supports the rack gears 7 is not illustrated.

As shown in FIG. 1, in a plan view, the two rack gears 7 are disposed so that teeth 7a thereof face each other, and, as shown in FIG. 2, in a side view, the two rack gears 7 are disposed at different positions in the thickness direction.

Figure 5A:
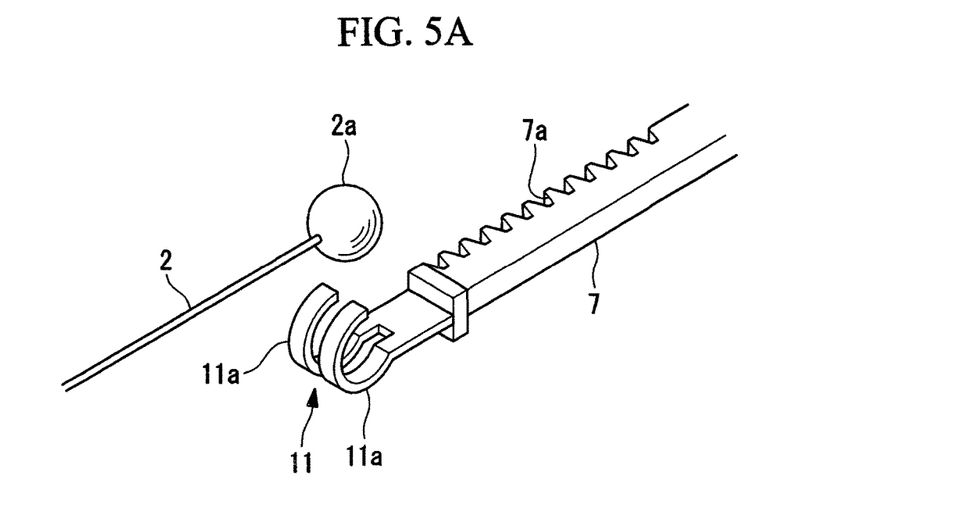
FIG. 5A is a perspective view for explaining attachment of a wire of the treatment tool to the treatment-tool driving device in FIG. 1, showing a state during attachment of the wire.

As shown in FIG. 5A, a hook 11 having two claws is attached to an end portion of each of the rack gears 7. The two claws 11a of the hook 11 are arranged with a space therebetween, the size thereof being greater than the diameter of the wire 2 and smaller than the outer diameter of the spherical body 2a. By doing so, as shown in FIG. 5B, the end portion of each of the wires 2 can be attached to the rack gear 7 by hooking the spherical body 2a on the claws 11a by making the wire 2 pass through between the claws 11a.

Figure 5B:
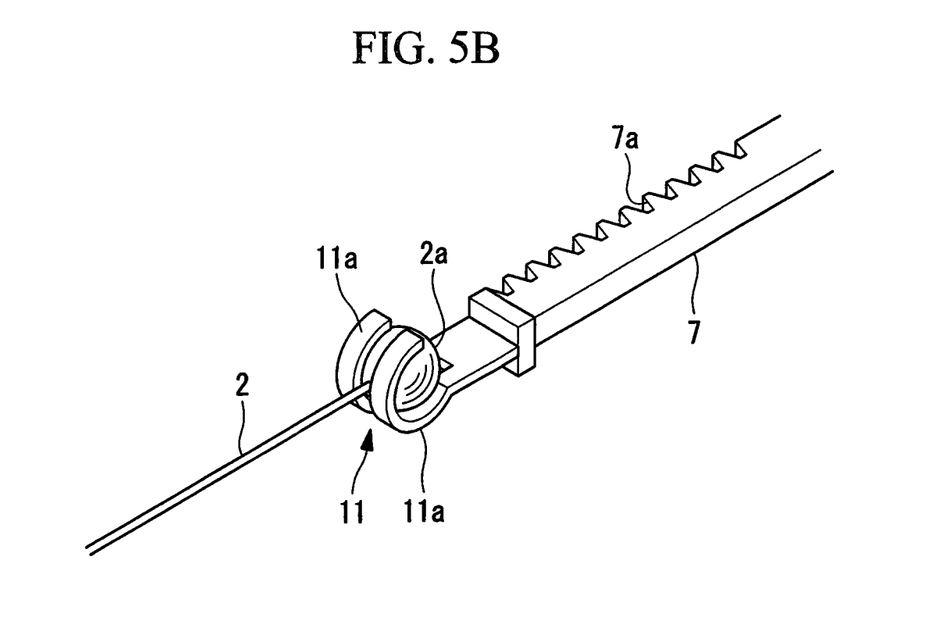
FIG. 5B is a perspective view for explaining attachment of the wire of the treatment tool to the treatment-tool driving device in FIG. 1, showing a state after attaching the wire.
Figure 6:
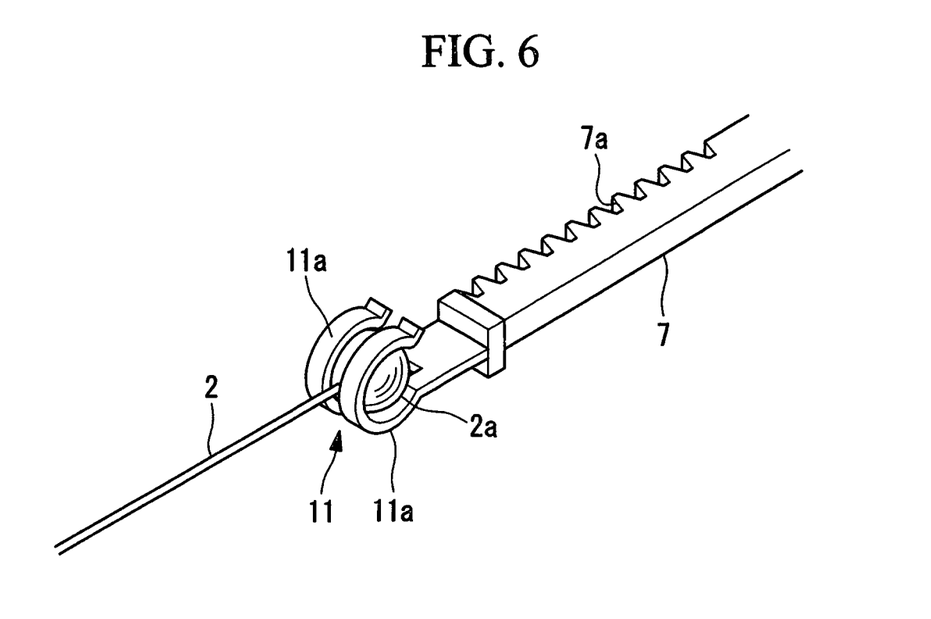
FIG. 6 is a perspective view showing a modification of a hook of the treatment-tool driving device in FIG. 1.

Note that, for the hook 11, a configuration that allows it to be easily removed may be employed, as shown in FIGS. 5A and 5B; selectively, as shown in FIG. 6, the entrance for the spherical body 2a between the two claws may be narrowly formed, the two claws may possess a spring property, and, when hooking the spherical body 2a into the hook 11, the spherical body 2a may be hooked by widening the entrance by elastically deforming the two claws by using the spherical body 2a. By doing so, it is possible to prevent the spherical body 2a from being dislodged from the hook 11 just because the wire is relaxed.

Figure 7:
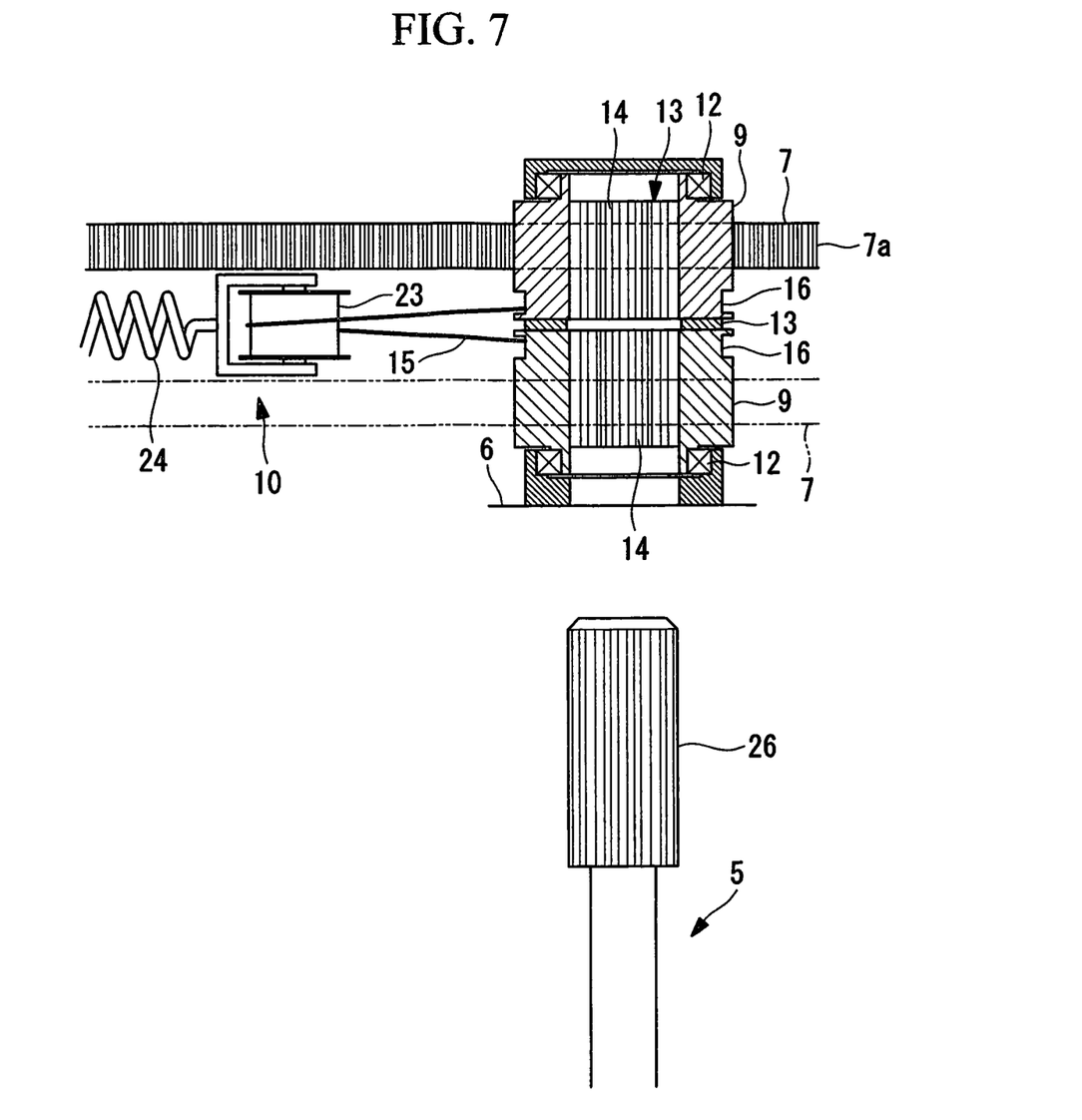
FIG. 7 is a partial longitudinal cross-sectional view showing a state before attaching the driving portion to an intermediate-mechanism portion of the treatment-tool driving device in FIG. 1.
Figure 8:
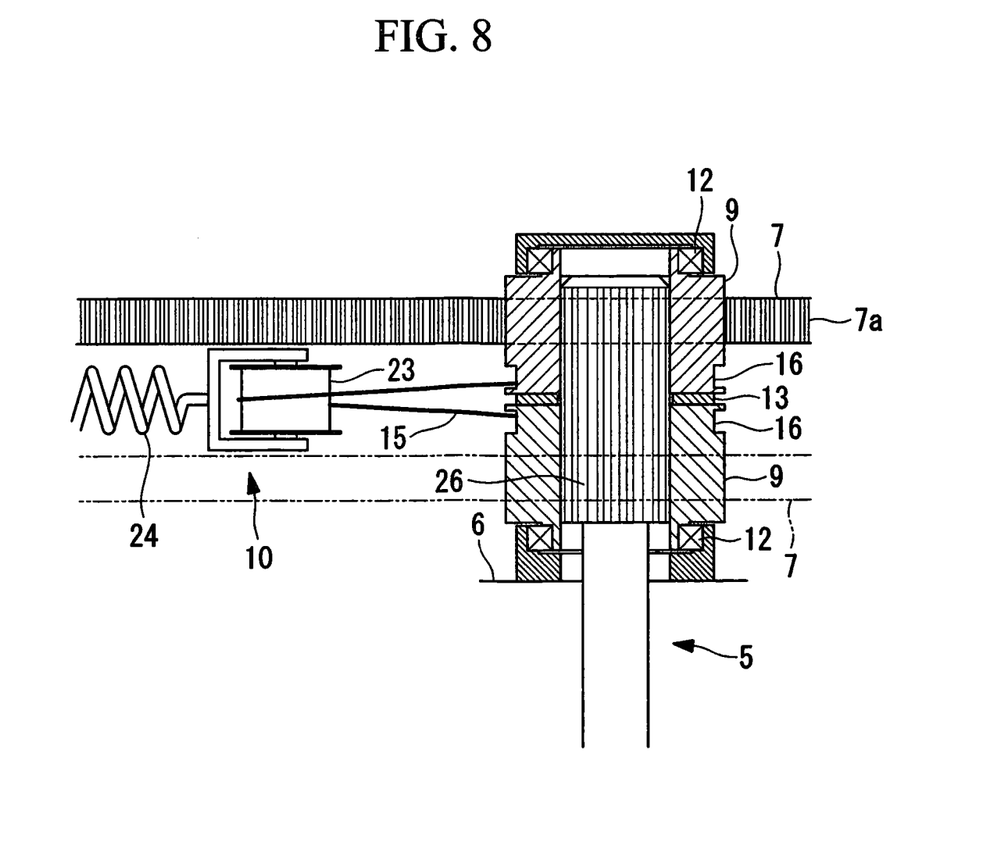
FIG. 8 is a partial longitudinal cross-sectional view showing a state after attaching the driving portion to the intermediate-mechanism portion of the treatment-tool driving device in FIG. 1.

As shown in FIGS. 2, 7, and 8, the two pinion gears (motive-power transmitting mechanisms) 9 are coaxially disposed, and are supported by the base 6 such that bearings 12 allow them to freely rotate relative to each other. The individual pinion gears 9 are disposed so as to engage with different rack gears 7. In the figures, the reference sign 13 is a spacer.

In the pinion gears 9, through-holes are formed at the centers thereof, and, in the circumferential direction, a plurality of spline grooves are formed in inner surfaces of the through-holes along the longitudinal direction, thus forming spline holes (fitting holes) 14. The spline holes 14 of the two pinion gears 9 have the same shape.

A pulley portion 16 around which a wire 15 of the biasing portion 10, described later, is wound is provided at a portion in the axial direction of each of the pinion gears 9.

The alignment mechanism 8 is provided with: guide rails 17 that are provided on the base 6 so as to be parallel to the rack gears 7; a slider 18 that is supported on the guide rails 17 so as to be linearly movable; and abutting members 19 provided on the slider 18. The slider 18 is provided with an operating lever 20 that protrudes toward one side of the base 6 in a width direction and that is operated by an operator.

The abutting members 19 are disposed at positions at which the abutting members 19 abut stepped sections 21 at end portions of the individual rack gears 7. By abutting the abutting members 19 against the stepped sections 21 by moving the slider 18, the end portions of the rack gears 7 are aligned.

Figure 4A:
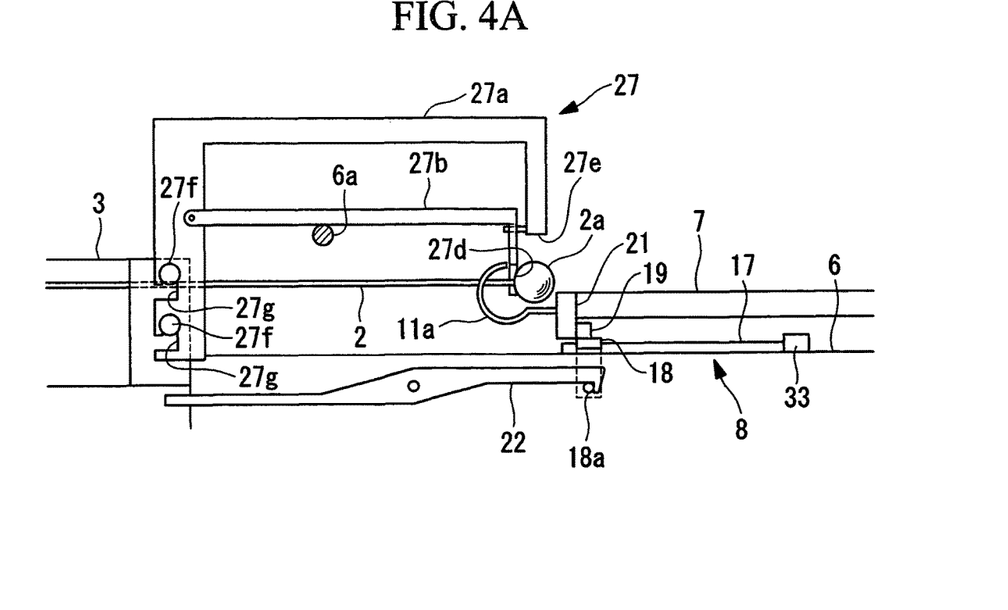
FIG. 4A is a partial front view for explaining a state before attaching the treatment tool, when attaching the treatment tool to the treatment-tool driving device in FIG. 1.
Figure 4B:
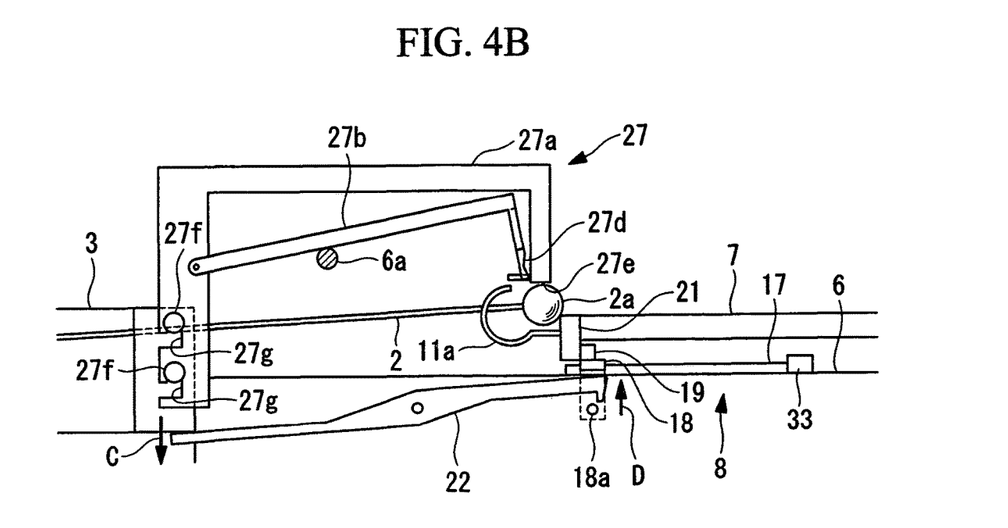
FIG. 4B is a partial front view for explaining a state during attachment of the treatment tool, when attaching the treatment tool to the treatment-tool driving device in FIG. 1.
Figure 4C:
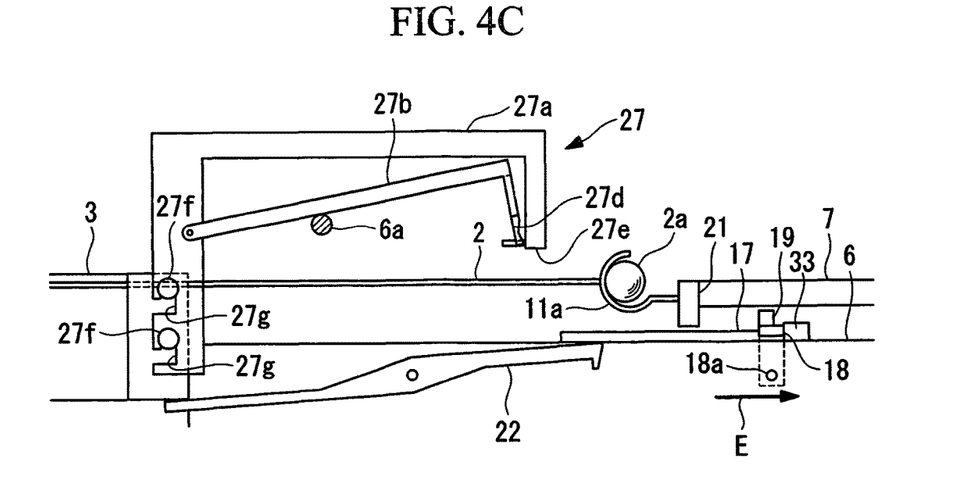
FIG. 4C is a partial front view for explaining a state after attaching the treatment tool, when attaching the treatment tool to the treatment-tool driving device in FIG. 1.

As shown in FIGS. 4A to 4C, the slider 18 is provided with an engagement protrusion (lock mechanism) 18a and is configured so as to be maintained in a stationary state at a position at which the rack gears 7 are moved closest to the hooks 11 by hooking the engagement protrusion 18a on a movable hook (lock mechanism) 22 at that position.

The biasing portion 10 is provided with: the wire (wire-like member) 15 that is wound around the pulley portions 16 provided at the two pinion gears 9; a movable pulley (pulley-like member) 23 for pulling an intermediate position in the length direction of the wire 15; and a spring (biasing member) 24 that is secured to the movable pulley 23 at one end thereof and that biases the movable pulley 23 in a direction in which a tensile force is imparted to the wire 15 (direction of the arrow A in the figure). The other end of the spring 24 is secured to the base 6.

One end of the wire 15 is secured after being wound around the pulley portion 16 of one of the pinion gears 9, and the other end of the wire 15 is secured after being wound around the pulley portion 16 of the other pinion gear 9. The winding directions of the wire 15 are such that the rack gears 7 engaged with the individual pinion gears 9 are moved in the direction of end portions on the opposite side from the end portions provided with the hooks 11 (direction of the arrow B).

In other words, because the pulley portion 16 around which the wire 15 is wound clockwise receives a counterclockwise rotational force when a tensile force is imparted to the wire 15, the pinion gear 9 is rotated counterclockwise, and thus, the rack gear 7 engaged therewith is moved in the direction of the arrow B. In addition, the pulley portion 16 around which the wire 15 is wound counterclockwise is configured so as to rotate the pinion gear 9 clockwise, thus moving the rack gear 7 engaged therewith in the direction of the arrow B.

The driving portion 5 is provided with a motor 25 and a spline shaft (fitting shaft) 26 that is rotated by the motor 25. In addition, the driving portion 5 can move the spline shaft 26 in the longitudinal direction by means of an insertion/extraction mechanism (not shown) and is configured so that it is possible to switch between a state in which the spline shaft 26 is extracted from the spline holes 14 of the pinion gears 9, as shown in FIG. 7, and a state in which the spline shaft 26 is inserted into the spline holes 14, as shown in FIG. 8.

Figure 3:
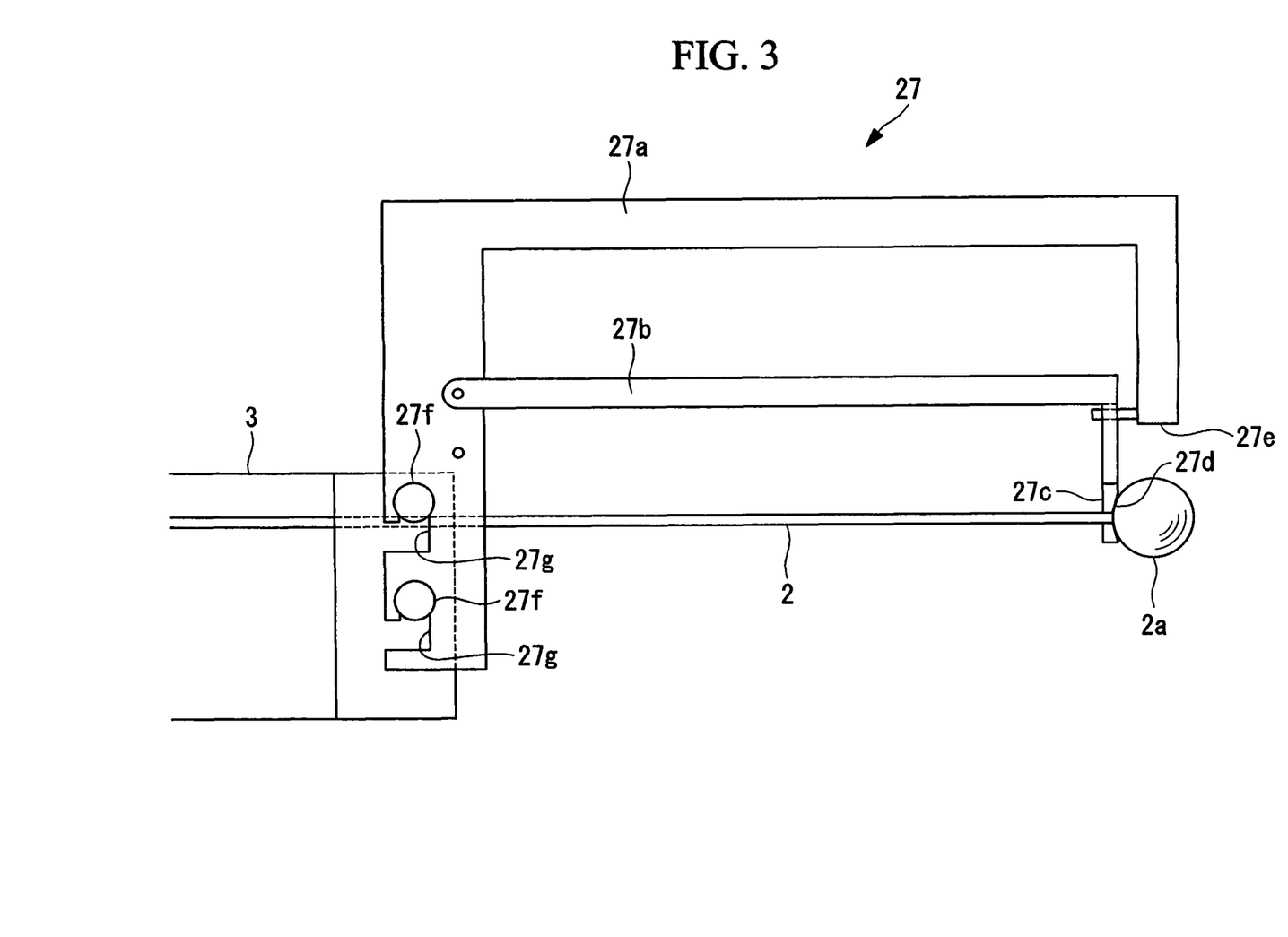
FIG. 3 is a front view for explaining a state in which a treatment tool is attached to the treatment-tool driving device in FIG. 1.

In order to attach the treatment tool 3 to the intermediate-mechanism portion 4, the treatment tool 3 is configured so as to be attached to the intermediate-mechanism portion 4 in a state in which the treatment tool 3 is attached to a wire support portion 27 that temporarily supports the wires 2. As shown in FIGS. 3 to 4C, the wire support portion 27 is provided with: a frame 27a that is attached to the treatment tool 3 in an attachable/detachable manner; and arms 27b that are attached to the frame 27a in a pivotable manner. In these figures, although only one wire 2 of the pair of wires 2 is illustrated to simplify the treatment tool 3, the other wire 2 is also supported by using the same method. The alignment mechanism 8 and the wire support portion 27 form a switch mechanism that switches between a supported state in which the wires 2 are supported by the wire support portion 27 and a coupled state in which the wires 2 are coupled with the hooks 11.

Each of the arms 27b is provided with, at the distal end thereof: a slit 27c in which the width thereof is larger than the outer diameter of the wire 2 and smaller than the diameter of the spherical body 2a; and a depression 27d that brings the spherical body 2a into stable contact. In a state in which the arm 27b is disposed as shown in FIG. 3, the spherical body 2a is disposed in the depression 27d by passing the wire 2 through the slit 27c, and thus, the wire 2 is held in a state in which the wire 2 is extended without slack.

The arms 27b are provided so as to be pivotable in one direction with respect to the frame 27a, and the distal end of the frame 27a is provided with stoppers 27e that, when the spherical bodies 2a supported at the distal ends of the arms 27b are moved due to pivoting of the arms 27b, block the movements of the spherical bodies 2a by abutting against the spherical bodies 2a, thus causing them to be dislodged from the depressions 27d. The reference signs 27f and 27g respectively indicate a protrusion and a groove for attaching/detaching the frame 27a to/from the treatment tool 3.

In addition, the treatment tool 3 is configured so as to be attached to the base 6 while being moved in a direction orthogonal to a surface of the base 6, and is configured so that, during this movement, the locked state between the movable hook 22 and the engagement protrusion 18a of the slider 18 is released by pressing the movable hook 22.

In addition, as shown in FIGS. 4A to 4C, the base 6 is provided with abutting members 6a for pivoting the arms 27b by means of a motion in a direction orthogonal to the surface of the base 6 when attaching the treatment tool 3 thereto.

The operation of the thus-configured treatment-tool driving device 1 according to this embodiment will be described below.

In order to attach the treatment tool 3 to the treatment-tool driving device 1 according to this embodiment, the slider 18 is moved by operating the operating lever 20 of the intermediate-mechanism portion 4 in a state in which the driving portion 5 is separated. By doing so, the abutting members 19 provided in the slider 18 are abutted against the stepped sections 21, and thus, the two rack gears 7 are moved toward the hooks 11 while being aligned.

The rack gears 7 are engaged with the pinion gears 9; because the pinion gears 9 are connected with the biasing portion 10, when the rack gears 7 are moved, the pinion gears 9 are rotated in the direction in which the wire 15 is taken up by the pulley portion 16, thus moving the movable pulley 23; and, by doing so, the spring 24 is stretched, thus increasing the biasing force thereof. The operator can align the positions of the hooks 11 at the end portions of the two rack gears 7 by moving the operating lever 20 against this biasing force. In addition, as shown in FIG. 4A, the slider 18 is locked at a position at which the rack gears 7 are moved closest to the hooks 11 by hooking the engagement protrusion 18a provided in the slider 18 on the movable hook 22 provided in the base 6 at that position.

In addition, as shown in FIG. 3, the wire support portion 27 is attached to the treatment tool 3. In other words, the frame 27a is attached to the treatment tool 3, and the spherical bodies 2a at the distal ends of the wires 2 are accommodated in the depressions 27d at the distal ends of the arms 27b by making the wires 2 pass through the slits 27c at the distal ends of the arms 27b. By doing so, as shown in FIG. 3, the wires 2 are kept in a state in which the wires 2 extend without slack.

The treatment tool 3 prepared in this way is attached to the intermediate-mechanism portion 4, as shown in FIGS. 4A to 4C. In other words, the treatment tool 3 in which the wires 2 are supported without slack by using the wire support portion 27 is brought close to the intermediate-mechanism portion 4 in which the hooks thereof are aligned, and thus, the treatment tool 3 is placed at a position at which the spherical bodies 2a are hooked in the hooks 11, as shown in FIG. 4A. At this point, the abutting members 6a provided in the base 6 are abutted against the arms 27b.

Then, as indicated by the arrow C in FIG. 4A, when the treatment tool 3 is brought even closer to the intermediate-mechanism portion 4, the arms 27b are pivoted by the abutting members 6a. Although the spherical bodies 2a supported by the arms 27b are also pivoted together therewith, because the stoppers 27e provided in the frame 27a abut against the spherical bodies 2a, the spherical bodies 2a are dislodged from the depressions of the arms 27b, thus being released into the hooks 11. Simultaneously with this, the treatment tool 3 presses the movable hook 22, which causes the movable hook 22 to pivot as indicated by the arrow D, and thus, the engagement with the engagement protrusion 18a is released.

By doing so, as indicated by the arrow E in FIG. 4C, because the rack gears 7 are moved, due to the biasing force of the biasing portion 10, in the direction in which the hooks 11 are pulled, initial tensile forces in accordance with the biasing force are imparted to the wires 2 in which the spherical bodies 2a are engaged with the hooks 11. At this time, although the two pinion gears 9 that individually engage with the two rack gears 7 are rotated in the direction in which the wire 15 wound around the respective pulley portions 16 is let out, because the wire 15 is continuous via the movable pulley 23, the movable pulley 23 is rotated so as to balance the tensile force therein and is stopped at a position at which a balance is achieved between the tensile forces in the wires 2 of the treatment tool 3 and the tensile force in the wire 15 of the biasing portion 10. At this time, the slider 18 is moved to the position of stoppers 33 by means of a spring (not shown), and the engagement between the abutting members 19 and the stepped sections 21 is released.

In this state, as shown in FIGS. 7 and 8, the frame 27a is removed from the treatment tool 3, and the spline shaft 26 of the driving portion 5 is inserted into and engaged with the spline holes 14 formed in the two pinion gears 9. By doing so, the two pinion gears 9 are coupled with each other, and thus, the driving force from the motor 25 is transmitted to the two pinion gears 9. Therefore, by means of the driving of the motor 25, the two pinion gears 9 are rotated in the same direction, and the rack gears 7 disposed so as to be parallel to each other on either side of the pinion gears 9 are moved in mutually opposing directions.

In other words, the tensile force is imparted to the wire 2 of the treatment tool 3 to which one of the rack gears 7 is connected, and the tensile force in the wire 2 to which the other rack gear 7 is connected is relaxed. As a result, it is possible to selectively impart tensile forces to the pair of wires 2 of the treatment tool 3 by means of the driving of the motor 25. By doing so, it is possible to drive joints or the like of the treatment tool 3.

In this case, with the treatment-tool driving device 1 according to this embodiment, because the wire 15 of the biasing portion 10 is threaded around the movable pulley 23, when the pinion gears 9 are being rotated by means of the driving of the motor 25, the wire 15 taken up by the pulley portion 16 of one of the pinion gears 9 is taken up by the pulley portion 16 of the other pinion gear 9 by the same length. Therefore, the position of the movable pulley 23 does not change after inserting the spline shaft into the spline holes, and thus, it is possible to put the biasing portion 10 in a state in which movements of the rack gears 7 are disengaged therefrom.

With the treatment-tool driving device 1 according to this embodiment, because the initial tensile forces are automatically imparted to the pair of wires 2 of the treatment tool 3 when attaching the treatment tool 3 to the intermediate-mechanism portion 4, it is not necessary to separately adjust tensile forces in the plurality of wires 2 of the treatment tool 3, and thus, there is an advantage in that it is possible to eliminate time and work required for performing the adjustments. Although this embodiment has been described by using a case in which there are two wires 2, which form a pair, as an example, in the case in which the treatment tool 3 is provided with multiple pairs of wires 2 also, it is possible to simultaneously impart initial tensile forces to all wires 2 in the same manner, thus making it possible to additionally and considerably reduce the time and work involved therein.

In addition, because the spherical bodies 2a of the wires 2 are simply hooked in the hooks 11 attached to the rack gears 7, there is an advantage in that, when removing the treatment tool 3 from the treatment-tool driving device 1 also, the treatment tool 3 can easily be removed by removing the spherical bodies 2a from the hooks 11.

Note that, in this embodiment, although a case in which the treatment tool 3 is driven by the pair of wires 2 has been described, the tensile-force transmitting members are not limited to the wires 2, and belts, tubes, or members that can transmit not only tensile forces but also pressing forces may be employed.

In addition, in the case in which the treatment tool 3 has a plurality of joints or the like, and is driven by multiple pairs of wires 2, initial tensile forces may be adjusted so that the joints individually have different initial tensile forces.

In addition, the movable pulley 23 or the pulley portions 16 around which the wire 15 is wound may be a columnar body having a cylindrical surface that does not rotate. By allowing the wire 15 to slide along the cylindrical surface, it is possible to achieve the same effects.

In addition, although the spherical bodies 2a and the hooks 11 have been described as examples of structures that couple the wires 2 and the rack gears 7, alternatively, arbitrary connecting structures may be employed.

Figure 9:
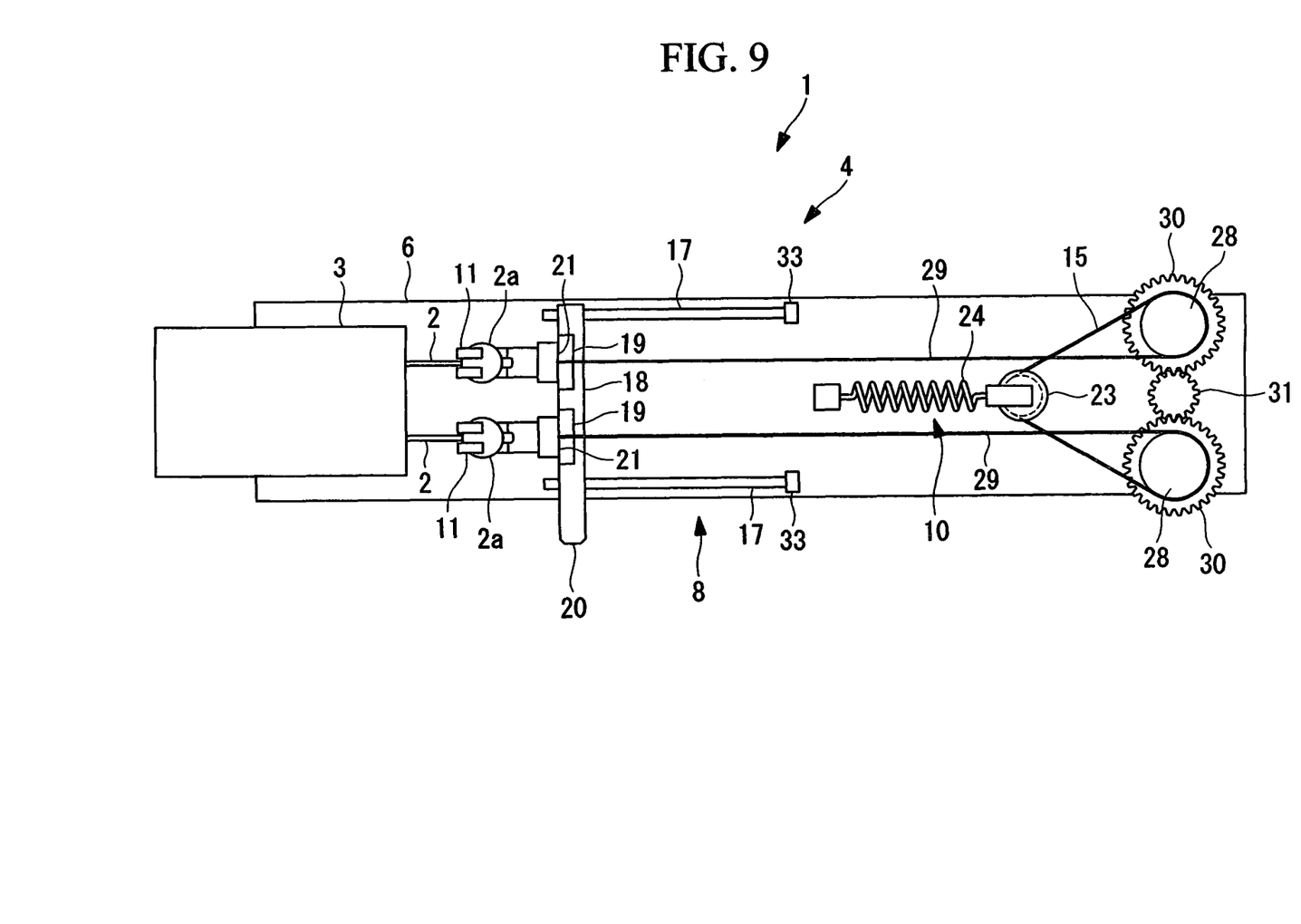
FIG. 9 is a plan view showing a first modification of the treatment-tool driving device in FIG. 1.

In addition, in this embodiment, although the rack gears 7 have been employed as the movable members of the intermediate-mechanism portion 4 that are coupled with the wires 2 of the treatment tool 3, selectively, as shown in FIG. 9, wires 29 that are wound around pulleys 28 may be employed. In this case, a mechanism provided with driven spur gears 30 secured to the pulleys 28 and a driving spur gear 31 that is rotated by the motor 25 may be employed as a driving-force transmitting mechanism.

By employing such a configuration, in a state in which the driving spur gear 31 is not engaged with the driven spur gears 30, the two driven spur gears 30 and the pulleys 28 secured thereto are freely rotatable, and thus, it is possible to allow them to freely rotate until reaching positions at which the tensile forces in the wires 29 are balanced in accordance with the biasing force of the biasing portion 10. Then, by inserting the driving spur gear 31 between the two driven spur gears 30 and by engaging them in the state in which the tensile forces are balanced, the influence of the biasing force of the biasing portion 10 is removed, and thus, it becomes possible to selectively impart tensile forces to the two wires 29.

Figure 10:
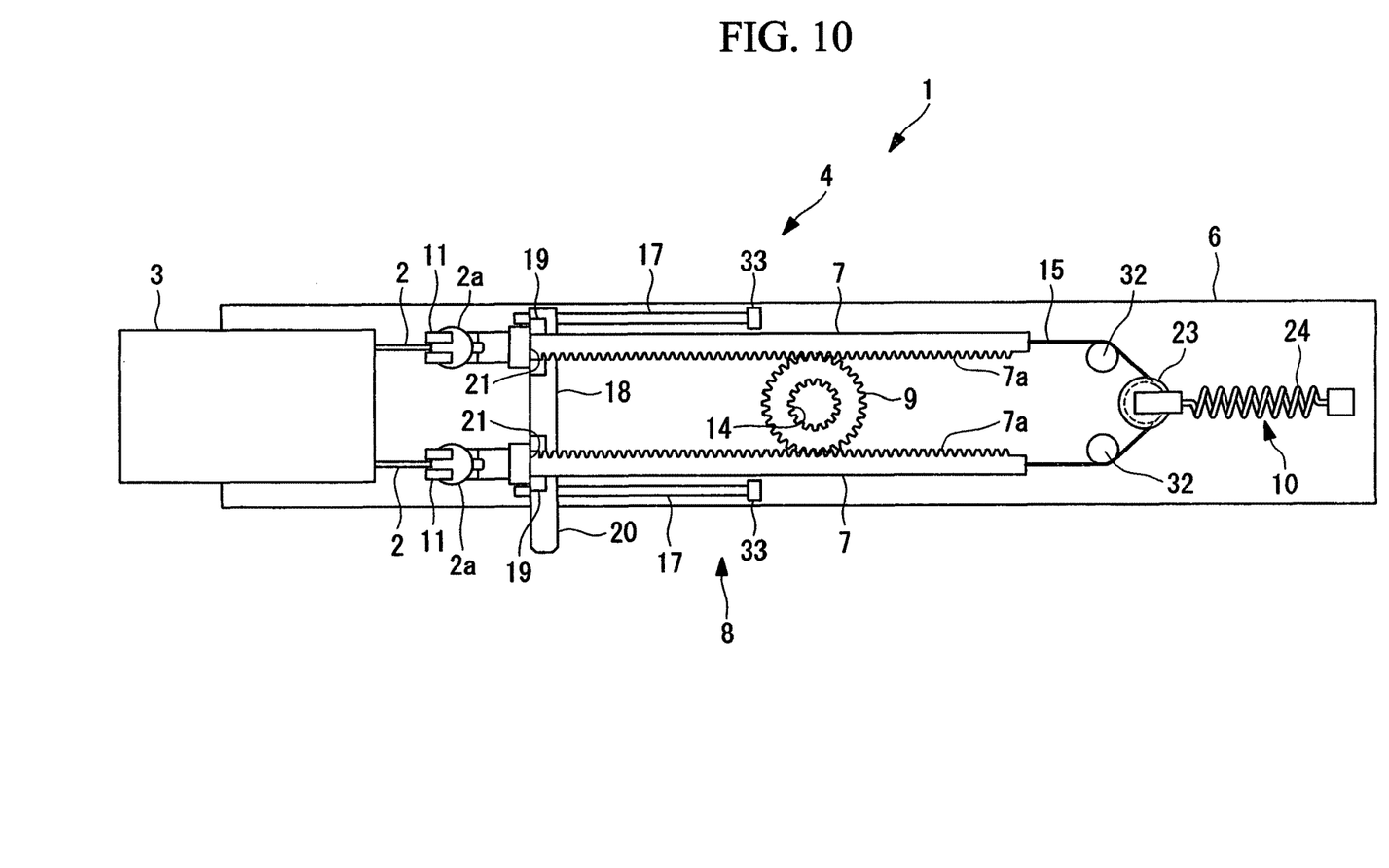
FIG. 10 is a plan view showing a second modification of the treatment-tool driving device in FIG. 1.

In addition, although the biasing portion 10 is assumed to apply rotational forces to the pulley portions 16 provided in the pinion gears 9, as shown in FIG. 10, one that directly applies tensile forces to the rack gears 7 may be employed. The reference sign 32 is a stationary pulley. In addition, the pinion gears 9 in FIG. 10 may be eliminated, a pinion gear may be employed instead of the spline shaft 26 of the driving portion 5, and the pinion gear may be directly inserted/extracted into/from the space between the rack gears 7.

The above-described embodiment leads to the following inventions.

An aspect of the present invention is a treatment-tool driving device that is attached, in an attachable/detachable manner, to a treatment tool provided with at least one pair of tensile-force transmitting members and that drives the treatment tool by means of tensile forces imparted to the tensile-force transmitting members, the treatment-tool driving device including: movable members that are individually attached, in an attachable/detachable manner, to one ends of the individual tensile-force transmitting members; a driving source that generates motive power with which the treatment tool is driven; a motive-power transmitting mechanism that switches between coupling and decoupling between the driving source and the movable members, and that transmits, in a coupled state, the motive power from the driving source so as to selectively impart tensile forces to the two movable members attached to the paired tensile-force transmitting members; and a biasing portion that biases the two movable members in directions in which tensile forces are imparted to the tensile-force transmitting members in a state in which coupling by the motive-power transmitting mechanism is released.

With this aspect, when the movable members are attached to one ends of at least one pair of the tensile-force transmitting members provided in the treatment tool in a state in which coupling between the driving source and the movable members by the motive-power transmitting mechanism is released, as a result of the biasing portion biasing the movable members in one direction, tensile forces are imparted to the tensile-force transmitting members. In other words, in the state in which the coupling is released, initial tensile forces are imparted to the tensile-force transmitting members of the treatment tool. When the driving source is coupled with the movable members in this state, the motive power from the driving source is transmitted to the movable members by the motive-power transmitting mechanism, and, as a result of actuation of the driving source selectively imparting tensile forces to the two movable members, the tensile forces are selectively imparted to the paired tensile-force transmitting members of the treatment tool, thus making it possible to drive the treatment tool.

In this case, when a state in which the motive power from the driving source is transmitted to the movable members is established, it is possible to achieve a state in which the initial tensile forces are imparted to the plurality of tensile-force transmitting members of the treatment tool. Therefore, it is not necessary to perform adjustment procedures for separately imparting tensile forces to the plurality of tensile-force transmitting members, and thus, it is possible to reduce the time and work involved therein. In addition, it is possible to precisely actuate the treatment tool without causing a time delay starting from an initial actuation after attaching the treatment tool.

The above-described aspect may be provided with an intermediate-mechanism portion that is coupled with the treatment tool in an attachable/detachable manner, wherein the intermediate-mechanism portion is provided with: the movable members; the motive-power transmitting mechanism; and the biasing portion, and wherein the motive-power transmitting mechanism switches between coupling and decoupling between the driving source and the movable members by attaching/detaching the driving source to/from the intermediate-mechanism portion.

By doing so, when the treatment tool is attached to the intermediate-mechanism portion to which the driving source is not attached, the movable members of the intermediate-mechanism portion are individually attached to one ends of at least one pair of the tensile-force transmitting members provided in the treatment tool, and, as a result of the biasing portion biasing the movable members in one direction, tensile forces are imparted to the tensile-force transmitting members. In other words, in a state in which the driving source is not attached, the initial tensile forces are imparted to the tensile-force transmitting members of the treatment tool. When the driving source is attached to the intermediate-mechanism portion in this state, the motive power from the driving source is transmitted to the movable members by the motive-power transmitting mechanism, and, as a result of actuation of the driving source selectively imparting tensile forces to the two movable members, the tensile forces are selectively imparted to the paired tensile-force transmitting members of the treatment tool, thus making it possible to drive the treatment tool.

In this case, when attaching the driving source to the intermediate-mechanism portion, it is possible to achieve a state in which the initial tensile forces are imparted to the plurality of tensile-force transmitting members of the treatment tool. Therefore, it is not necessary to perform adjustment procedures for separately imparting tensile forces to the plurality of tensile-force transmitting members, and thus, it is possible to reduce the time and work involved therein. In addition, it is possible to precisely actuate the treatment tool without causing a time delay starting from an initial actuation after attaching the treatment tool.

In the above-described aspect, the driving source may be a motor, the two movable members may be two rack gears that are supported substantially parallel to each other so as to be individually movable in longitudinal directions and so that teeth thereof face each other, and the motive-power transmitting mechanism may engage with both of the two rack gears, and may be provided with pinion gears that move the two rack gears in opposite directions by means of driving of the motor.

By doing so, by applying the motive power of the motor to the pinion gears engaged with the two rack gears in a state in which the two rack gears are biased in one direction by the biasing portion and tensile forces are imparted to the tensile-force transmitting members of the treatment tool, it is possible to drive the treatment tool by selectively imparting tensile forces to the paired tensile-force transmitting members by moving the rack gears in opposite directions. Because tensile forces are imparted to the tensile-force transmitting members when driving, it is possible to precisely control the treatment tool.

In the above-described aspect, the pinion gears may be separately provided for the rack gears and are disposed coaxially with each other in a freely rotatable manner, and the motive-power transmitting mechanism may be provided with: fitting holes provided in the individual pinion gears; and a fitting shaft that is secured to the motor and that is fitted to the fitting holes provided in the two pinion gears to couple the two pinion gears.

By doing so, in a state in which the fitting shaft on the motor is not fitted to the fitting holes of the two pinion gears, the two pinion gears can be freely rotated, thus allowing movement of the rack gears engaged therewith, and it is possible to separately adjust tensile forces for the two tensile-force transmitting members. In addition, in a state in which the fitting shaft on the motor is fitted to the fitting holes of the two pinion gears, the two pinion gears are coupled with each other, and thus, it is possible to drive the treatment tool by selectively imparting tensile forces to the two tensile-force transmitting members by means of driving of the motor.

In the above-described aspect, the biasing portion may be provided with: a flexible wire-like member that is individually secured at the two ends thereof so as to impart rotational forces to the two pinion gears by means of a tensile force; a pulley-like member around which the wire-like member is wound at an intermediate position thereof; and a biasing member that imparts a tensile force to the wire-like member by biasing the pulley-like member in a radial direction.

By doing so, when the biasing member biases the pulley-like member in a radial direction, the wire-like member wound around the pulley-like member at the intermediate position thereof is pulled and a tensile force is generated, and, as a result of the two pinion gears being rotated, the rack gears engaged with the pinion gears are moved in the longitudinal direction, thus imparting the initial tensile forces to the tensile-force transmitting members of the treatment tool. When the two pinion gears are coupled with the motor by fitting the fitting shaft in the fitting holes in this state and when the motor is subsequently actuated, the wire-like member is moved in a longitudinal direction via the pulley-like member, and thus, the wire-like member is taken up toward one of the pinion gears and is let out from the other pinion-gear side. At this time, because the position of the pulley-like member does not change, the tensile force imparted to the wire-like member does not change regardless of the positions of the rack gears, making it possible to simplify the control of the treatment tool.

In the above-described aspect, the driving source may be a motor, the two movable members may be wire-like members, and the motive-power transmitting mechanism may be provided with: two pulley-like members around which the two wire-like members are individually wound; driven gears that are coaxially secured to the individual pulley-like members; and a driving gear that is provided so as to allow insertion/extraction thereof into/from a position at which the driving gear simultaneously engages with the individual driven gears, and that, in an engaged state, moves the two wire-like members in opposite directions by means of driving of the motor.

By doing so, by applying the motive power to the pulley-like members around which the wire-like members are wound by engaging the driving gear with the two driven gears in a state in which the two wire-like members are biased in one direction by the biasing portion and tensile forces are imparted to the tensile-force transmitting members of the treatment tool, it is possible to selectively impart tensile forces to the paired tensile-force transmitting members by moving the two wire-like members in opposite directions. Because tensile forces are imparted to the tensile-force transmitting members when driving, it is possible to precisely control the treatment tool.

In the state in which the driving gear is not engaged with the driven gears, the two pulley-like members are freely rotated, thus allowing movement of the wire-like members, and it is possible to separately adjust the tensile forces for the two tensile-force transmitting members. In addition, in the state in which the driving gear is engaged with the two driven gears, the two pulley-like members work in association with the movement of the driving gear, and thus, it is possible to drive the treatment tool by selectively imparting tensile forces to the two tensile-force transmitting members by means of the driving of the motor.

The above-described aspect may be provided with a treatment-tool-side support portion that is attached to the treatment tool in an attachable/detachable manner and that holds a plurality of the tensile-force transmitting members in a state in which positions thereof are set, wherein the intermediate-mechanism portion is provided with an alignment mechanism that holds the plurality of movable members in an aligned state at positions at which the movable members are coupled with the tensile-force transmitting members, and wherein a switch mechanism is provided, which, when attaching the treatment tool to the intermediate-mechanism portion, releases the state in which the tensile-force transmitting members are held by the treatment-tool-side support portion, and which couples one ends of the tensile-force transmitting members with the movable members that are aligned by means of the alignment mechanism.

By doing so, when attaching, to the intermediate-mechanism portion at which the movable members are aligned by the alignment mechanism, the treatment tool with which the tensile-force transmitting members are held in a state in which the positions thereof are set at the treatment-tool-side support portion, because the state in which the tensile-force transmitting members are held by the treatment-tool-side support portion is released by the switch mechanism and the tensile-force transmitting members are coupled with the movable members at one ends thereof, it is possible to collectively couple the plurality of tensile-force transmitting members at a time, and thus, it is possible to reduce the time and work involved when attaching them.

In the above-described aspect, the alignment mechanism may be provided with: a slider that moves the plurality of movable members against a biasing force imparted thereto by the biasing portion; and a lock mechanism that locks the slider so as to place the movable members at coupling positions, wherein the switch mechanism releases the state in which the slider is locked by the lock mechanism in a state in which the tensile-force transmitting members are coupled with the movable members.

By doing so, the plurality of movable members are moved against the biasing force imparted thereto by the biasing portion when the slider is moved, and thus, the slider is locked at a coupling position by the lock mechanism. Then, when the treatment tool supported by the treatment-tool-side support portion is attached to the intermediate-mechanism portion, the state in which the slider is locked by the lock mechanism is released by the switch mechanism, and thus, it is possible to couple the movable members and the tensile-force transmitting members in a state in which the tensile force generated by the biasing portion is imparted to the tensile-force transmitting members via the movable members.

In the above-described aspect, the slider may be provided with another biasing portion that applies a biasing force in the same direction as the biasing force applied by the biasing portion.

By doing so, after the state in which the slider is locked by the lock mechanism is released, the slider is moved by the other biasing portion in a direction away from the movable members, and, thereafter, it is possible to prevent the movement of the movable members from being affected.

REFERENCE SIGNS LIST 1 treatment-tool driving device
2 wire (tensile-force transmitting member)
3 treatment tool
4 intermediate-mechanism portion
7 rack gear (movable member)
8 alignment mechanism
9 pinion gear (motive-power transmitting mechanism)
10 biasing portion
14 spline hole (fitting hole)
15 wire (wire-like member)
18 slider
18a engagement protrusion (lock mechanism)
22 movable hook (lock mechanism)
23 movable pulley (pulley-like member)
24 spring (biasing member)
25 motor (driving source)
26 spline shaft (fitting shaft)
27 wire support portion (treatment-tool-side support portion)
29 wire (movable member)
30 driven spur gear (driven gear)
31 driving spur gear (driving gear)

The invention claimed is:

1. A treatment-tool driving device that is attached, in an attachable/detachable manner, to a treatment tool provided with at least one pair of tensile-force transmitting members and that drives the treatment tool by means of tensile forces imparted to the tensile-force transmitting members, the treatment-tool driving device comprising:
    movable members each of which is attached, in an attachable/detachable manner, to one end of each of the tensile-force transmitting members;
    a driving source that generates motive power with which the treatment tool is driven;
    a motive-power transmitting mechanism that switches between coupling and decoupling between the driving source and the movable members, and that transmits, in a state in which the driving source and the movable members are coupled with each other, the motive power from the driving source so as to selectively impart tensile forces to the two movable members attached to the paired tensile-force transmitting members
    a biasing portion that biases the two movable members in directions in which tensile forces are imparted to the tensile-force transmitting members in a state in which the driving source and the movable members are decoupled from each other;
    an intermediate-mechanism portion that is coupled with the treatment tool in an attachable/detachable manner,
    wherein the intermediate-mechanism portion is provided with:
        the movable members;
        the motive-power transmitting mechanism; and
        the biasing portion,
    wherein the motive-power transmitting mechanism switches between coupling and decoupling between the driving source and the movable members by attaching/detaching the driving source to/from the intermediate-mechanism portion,
    wherein the driving source is a motor, wherein the two movable members are two rack gears that are supported substantially parallel to each other so as to be individually movable in longitudinal directions and so that teeth thereof face each other, and wherein the motive-power transmitting mechanism engages with both of the two rack gears, and is provided with pinion gears that move the two rack gears in opposite directions by means of driving of the motor.

2. The treatment-tool driving device according to claim 1, wherein the pinion gears are separately provided for the rack gears and are disposed coaxially with each other in a freely rotatable manner, and the motive-power transmitting mechanism is provided with:
fitting holes provided in the individual pinion gears; and
a fitting shaft that is secured to the motor and that is fitted to the fitting holes provided in the two pinion gears to couple the two pinion gears.

3. The treatment-tool driving device according to claim 1, wherein the biasing portion is provided with:
a flexible wire that is individually secured at the two ends thereof so as to impart rotational forces to the two pinion gears by means of a tensile force;
a pulley around which the wire is wound at an intermediate position thereof; and
a biasing member that imparts a tensile force to the wire by biasing the pulley in a radial direction.

4. A treatment-tool driving device that is attached, in an attachable/detachable manner, to a treatment tool provided with at least one pair of tensile-force transmitting members and that drives the treatment tool by means of tensile forces imparted to the tensile-force transmitting members, the treatment-tool driving device comprising:
movable members each of which is attached, in an attachable/detachable manner, to one end of each of the tensile-force transmitting members;
a driving source that generates motive power with which the treatment tool is driven;
a motive-power transmitting mechanism that switches between coupling and decoupling between the driving source and the movable members, and that transmits, in a state in which the driving source and the movable members are coupled with each other, the motive power from the driving source so as to selectively impart tensile forces to the two movable members attached to the paired tensile-force transmitting members;
a biasing portion that biases the two movable members in directions in which tensile forces are imparted to the tensile-force transmitting members in a state in which the driving source and the movable members are decoupled from each other; and
an intermediate-mechanism portion that is coupled with the treatment tool in an attachable/detachable manner,
wherein the intermediate-mechanism portion is provided with:
the movable members;
the motive-power transmitting mechanism; and
the biasing portion,
wherein the motive-power transmitting mechanism switches between coupling and decoupling between the driving source and the movable members by attaching/detaching the driving source to/from the intermediate-mechanism portion,
wherein the driving source is a motor,
wherein the two movable members are wires, and wherein the motive-power transmitting mechanism is provided with:
two pulleys around which the two wires are individually wound;
driven gears that are coaxially secured to the individual pulley; and
a driving gear that is provided so as to allow insertion/extraction thereof into/from a position at which the driving gear simultaneously engages with the individual driven gears, and that, in an engaged state, moves the two wires in opposite directions by means of driving of the motor.

5. A treatment-tool driving device that is attached, in an attachable/detachable manner, to a treatment tool provided with at least one pair of tensile-force transmitting members and that drives the treatment tool by means of tensile forces imparted to the tensile-force transmitting members, the treatment-tool driving device comprising:
movable members each of which is attached, in an attachable/detachable manner, to one end of each of the tensile-force transmitting members;
a driving source that generates motive power with which the treatment tool is driven;
a motive-power transmitting mechanism that switches between coupling and decoupling between the driving source and the movable members, and that transmits, in a state in which the driving source and the movable members are coupled with each other, the motive power from the driving source so as to selectively impart tensile forces to the two movable members attached to the paired tensile-force transmitting members;
a biasing portion that biases the two movable members in directions in which tensile forces are imparted to the tensile-force transmitting members in a state in which the driving source and the movable members are decoupled from each other; and
an intermediate-mechanism portion that is coupled with the treatment tool in an attachable/detachable manner,
wherein the intermediate-mechanism portion is provided with:
the movable members;
the motive-power transmitting mechanism; and
the biasing portion,
wherein the motive-power transmitting mechanism switches between coupling and decoupling between the driving source and the movable members by attaching/detaching the driving source to/from the intermediate-mechanism portion,
wherein the treatment-tool driving device further includes a treatment-tool-side support portion that is attached to the treatment tool in an attachable/detachable manner and that holds the tensile-force transmitting members in a state in which positions thereof are set,
wherein the intermediate-mechanism portion is provided with an alignment mechanism that holds the plurality of movable members in an aligned state at positions at which the movable members are coupled with the tensile-force transmitting members, and,
wherein a switch mechanism is provided, which, when attaching the treatment tool to the intermediate-mechanism portion, releases the state in which the tensile-force transmitting members are held by the treatment-tool-side support portion, and which couples one end of each of the tensile-force transmitting members with each of the movable members that is aligned by means of the alignment mechanism.

6. The treatment-tool driving device according to claim 5,
wherein the alignment mechanism is provided with:
- a slider that moves the plurality of movable members against a biasing force imparted thereto by the biasing portion; and
- a lock mechanism that locks the slider so as to place the movable members at coupling positions, wherein the switch mechanism releases the state in which the slider is locked by the lock mechanism in a state in which the tensile-force transmitting members are coupled with the movable members.

7. The treatment-tool driving device according to claim 6, wherein the slider is provided with another biasing portion that applies a biasing force in the same direction as the biasing force applied by the biasing portion.

* * * * *